US009205020B2

(12) United States Patent
Young et al.

(10) Patent No.: US 9,205,020 B2
(45) Date of Patent: Dec. 8, 2015

(54) MASSAGING MULTIPLE ROLLER-BALL APPLICATOR FOR TOPICAL OILS APPLICATION

(75) Inventors: D. Gary Young, Alpine, UT (US); Son Q. Le, Orem, UT (US); Marc F Schreuder, Provo, UT (US); Cole L. Woolley, Orem, UT (US)

(73) Assignee: Young Living Essential Oils, LC, Lehi, UT (US)

( * ) Notice: Subject to any disclaimer, the term of this patent is extended or adjusted under 35 U.S.C. 154(b) by 642 days.

(21) Appl. No.: 13/458,810

(22) Filed: Apr. 27, 2012

(65) Prior Publication Data

US 2013/0289457 A1    Oct. 31, 2013

(51) Int. Cl.
| | | |
|---|---|---|
| A61H 7/00 | (2006.01) | |
| A61H 15/00 | (2006.01) | |
| A61H 15/02 | (2006.01) | |
| A45D 34/04 | (2006.01) | |
| A61H 23/02 | (2006.01) | |
| A61M 35/00 | (2006.01) | |

(52) U.S. Cl.
CPC ............ *A61H 15/0078* (2013.01); *A61H 15/02* (2013.01); *A61H 23/0263* (2013.01); *A61H 2015/0064* (2013.01); *A61H 2015/0071* (2013.01); *A61M 35/003* (2013.01)

(58) Field of Classification Search
CPC ............ A61H 15/02; A61H 2201/105; A61H 2015/0071; A45D 34/00; A45D 34/04; A45D 34/041; A61M 35/003
USPC ............... 601/15, 17, 19, 154, 155, 160, 169; 401/28, 208–209; 222/129, 132, 142.8, 222/196
See application file for complete search history.

(56) References Cited

U.S. PATENT DOCUMENTS

| | | | | |
|---|---|---|---|---|
| 721,821 | A * | 3/1903 | Myers ........................... | 137/556 |
| 1,292,288 | A * | 1/1919 | Fisher ........................... | 401/280 |
| 1,947,042 | A * | 2/1934 | Glennan ................. | A61H 15/02 401/174 |
| 2,937,392 | A * | 5/1960 | Williams ....................... | 401/213 |
| 3,796,431 | A * | 3/1974 | Sinyard .............. | A63B 21/0618 482/108 |
| 4,037,977 | A * | 7/1977 | Ronai ........................... | 401/209 |
| 4,270,526 | A * | 6/1981 | Morales et al. ................ | 601/154 |

(Continued)

FOREIGN PATENT DOCUMENTS

| | | |
|---|---|---|
| KR | 20120007010 | 1/2012 |
| KR | 1020120007010 | 1/2012 |

OTHER PUBLICATIONS

Doterra Aromatics, "Orange, Wild (*Citrus sinensis*) Oil" and "Frankincense (*Boswellia frereana*) Oil", 2008-2009.*

(Continued)

*Primary Examiner* — Justine Yu
*Assistant Examiner* — Christopher Miller
(74) *Attorney, Agent, or Firm* — Kunzler Law Group, PC

(57) ABSTRACT

Exemplary massaging applicator devices for applying topical oils to an individual, such as a person or creature, and methods of applying topical oils are disclosed. Some embodiments of an exemplary massaging applicator device may include a body; a vibration assembly disposed within the body; at least one container configured to hold topical oil; and at least one roller-ball foot coupled to the body, wherein the container is in fluid communication with the at least one roller-ball foot such that the at least one roller-ball foot is configured to apply the topical oil. The topical oil may comprise an essential oil.

9 Claims, 6 Drawing Sheets

(56) References Cited

U.S. PATENT DOCUMENTS

| | | | |
|---|---|---|---|
| 4,326,508 A * | 4/1982 | Stauffer | 601/129 |
| 4,492,223 A * | 1/1985 | Burke | 601/154 |
| 4,571,106 A | 2/1986 | Scuderi | |
| 4,823,777 A * | 4/1989 | Goncalves et al. | 601/154 |
| 5,131,384 A * | 7/1992 | Obagi | 601/131 |
| 5,445,596 A * | 8/1995 | Grace | 601/154 |
| 5,934,296 A * | 8/1999 | Clay | 132/320 |
| 6,010,264 A * | 1/2000 | Scuderi et al. | 401/21 |
| 6,093,159 A * | 7/2000 | Racoosin | A61H 15/0092 601/118 |
| 6,896,161 B2 * | 5/2005 | Patz | B65D 47/246 222/484 |
| 6,911,010 B2 * | 6/2005 | Dirks et al. | 601/15 |
| 6,925,672 B1 * | 8/2005 | Bromley | 15/104.94 |
| 7,137,960 B2 * | 11/2006 | Tien | A61H 15/0092 601/118 |
| 7,293,930 B2 | 11/2007 | Chuang | |
| 7,311,462 B2 | 12/2007 | Kervoalen | |
| 7,425,102 B1 | 9/2008 | Velliquette | |
| 7,806,612 B1 * | 10/2010 | Wangler | 401/11 |
| 8,262,592 B1 * | 9/2012 | Brooks et al. | 601/17 |
| 8,714,853 B2 * | 5/2014 | Sutcliffe et al. | 401/28 |
| 2004/0149775 A1 * | 8/2004 | Chen | 222/135 |
| 2005/0169693 A1 | 8/2005 | Serio et al. | |
| 2005/0249540 A1 | 11/2005 | Gueret | |
| 2006/0018704 A1 | 1/2006 | Baines et al. | |
| 2006/0155225 A1 * | 7/2006 | Murdock et al. | 601/131 |
| 2006/0213926 A1 * | 9/2006 | Kraus | B65D 25/04 222/129 |
| 2006/0222445 A1 | 10/2006 | Chuang | |
| 2007/0083135 A1 * | 4/2007 | Gueret | 601/127 |
| 2007/0260159 A1 | 11/2007 | Cagle et al. | |
| 2008/0107474 A1 | 5/2008 | Hsieh | |
| 2008/0146977 A1 * | 6/2008 | Hilditch | 601/72 |
| 2008/0154161 A1 * | 6/2008 | Abbott | 601/113 |
| 2008/0248138 A1 | 10/2008 | Greco | |
| 2011/0066121 A1 * | 3/2011 | Hoang et al. | 604/310 |
| 2012/0177434 A1 * | 7/2012 | Geiger | A45D 40/261 401/216 |
| 2013/0101340 A1 * | 4/2013 | Liu | 401/208 |

OTHER PUBLICATIONS

PCT/US2012/035624, International Search Report, Jan. 24, 2013.

Application No. PCT/US2012/035624, International Preliminary Report on Patentability, Nov. 6, 2014.

U.S. Appl. No. 14/029,541, Office Action, May 5, 2015.

\* cited by examiner

MASSAGING MULTIPLE ROLLER-BALL APPLICATOR FOR TOPICAL OILS APPLICATION

FIELD

This application relates generally to massagers. In particular, this application relates to massagers with multiple roller-ball applicators for applying topical oils to an individual, such as a person or a creature.

BACKGROUND

In recent years, sales for essential oils and other topically applied oils have exploded. Topically applied oils are usually oils which are derived from, or include certain essential components or essences of different substances. Such topically applied oils are generally referred to as essential oils.

Essential oils, known as nature's living energy, are the natural, aromatic volatile liquids found in shrubs, flowers, trees, resins, fruit peels, rhizomes, roots, bushes, and seeds. The distinctive components in essential oils defend plants against insects, environmental conditions, and disease. They are also vital for a plant to grow, live, evolve, and adapt to its surroundings. Essential oils are extracted from aromatic plant sources via steam distillation, cold pressing, and other types of distillation. Essential oils are highly concentrated and far more potent than dry herbs. Other topically applied oils and fatty oils may include olive oil, almond oil, coconut oil, etc., and oils high in esters, such as jojoba oil, and waxes such as beeswax.

While essential oils often have a pleasant aroma, their phytochemical makeup is complex and their benefits vast—which makes them much more than something that simply smells good. Historically, essential oils have played a prominent ole in everyday life. With more than 200 references to aromatics, incense, and ointments throughout the Bible, essential oils are said to be used for anointing and healing the sick. Today, essential oils are used for aromatherapy, massage therapy, emotional health, personal care, nutritional supplements, household solutions, and much more.

Roller-ball applicators have been used in many applications. However, roller-ball applicators generally use a fairly pliable plastic housing to accommodate the ball in a press-fit assembly. Traditional roller-ball assemblies are unsuitable for use with most topical oils, such as essential oils, particularly citrus essential oils (i.e., lemon, orange, grapefruit, bitter orange, yuzu, lime, bergamot, etc.), frankincense, high terpene oils, and other similar oils that can have a potent solvent effect, because the oils tend to impregnate plastics and relax the elasticity or swell the plastic, which often causes the roller-ball to become excessively loose and potentially dislodge, or swell the roller-ball and generally make plastic containers unsuitable. Additionally, essential oils tend to work as solvents with many plastics and can leach unwanted chemicals, pigments, residual monomers, and compounds from the plastics into the essential oils. Because of this, applicators for topical oils use different application methods and devices that do not require plastics that retain their material properties, and when using essential oils, generally avoid plastics altogether.

SUMMARY

Exemplary massaging applicator devices for applying topical oils to an individual, such as a person or creature, and methods of applying topical oils are disclosed. Some embodiments of an exemplary massaging applicator device may include a body; a vibration assembly disposed within the body; at least one container configured to hold topical oil; and at least one roller-ball foot coupled to the body, wherein the container is in fluid communication with the at least one roller-ball foot such that the at least one roller-ball foot is configured to apply the topical oil. The topical oil may comprise an essential oil.

In some embodiments, the at least one roller-ball foot may include a retaining ring formed from metal, such as aluminum. Similarly, the at least one roller-ball foot may also include at least two or three, or more roller-ball feet. The vibration assembly may be configured to massage an individual contacting the at least one roller-ball foot. The fluid communication between the container and the roller-ball foot may be selectively closeable. The roller-ball is formed from metal or glass and may include surface features.

In some embodiments, topical oil may be applied to an individual by, placing topical oil in at least one container; coupling the at least one container to at least one roller-ball foot having a roller-ball; placing the roller-ball of the at least one roller-ball foot against the skin of an individual; applying massaging vibrations through the roller-ball to the individual; and moving the at least one roller-ball foot such that the roller-ball rotates within the at least one roller-ball foot and delivers oil to the skin of the individual. The topical oil in various containers may be an essential oil, such as a lavender, citrus, or frankincense, and may be different from the essential oil in another of the containers. In some embodiments, the at least one roller-ball foot may include a roller-ball housing, and wherein the roller-ball is held in the roller-ball housing with the retention cap.

BRIEF DESCRIPTION OF THE DRAWINGS

The following description can be better understood in light of Figures, in which.

Figure 1:
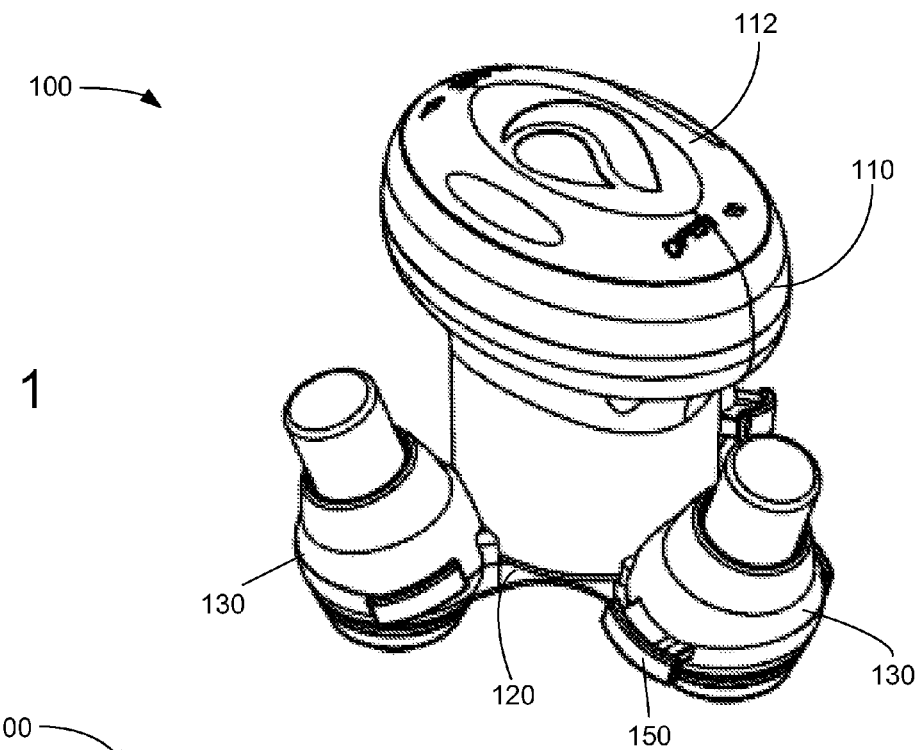
FIG. 1 illustrates an exemplary massaging multiple roller-ball topical oil applicator.

Together with the following description, the Figures demonstrate and explain the principles of massaging multiple roller-ball topical oil applicators and methods for making and using the massaging multiple roller-ball topical oil applicators. In the Figures, the thickness and configuration of components may be exaggerated for clarity. The same reference numerals in different Figures represent the same component.

DETAILED DESCRIPTION

The following description supplies specific details in order to provide a thorough understanding. Nevertheless, the skilled artisan would understand that the apparatus and associated methods of using the apparatus can be implemented and used without employing these specific details. Indeed, the apparatus and associated methods can be placed into practice by modifying the illustrated apparatus and associated methods and can be used in conjunction with any other apparatus and techniques conventionally used in the industry. For example, while the description below focuses on massaging multiple roller-ball applicators with three roller-balls, other numbers and configurations of roller-balls may be used.

Figure 2:
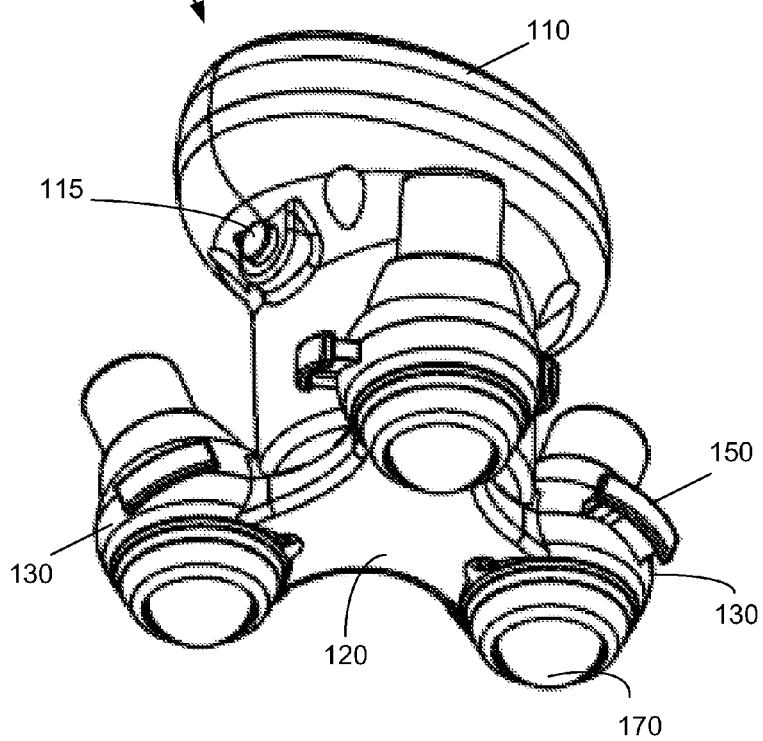
FIG. 2 illustrates an alternative perspective view of the exemplary massaging multiple roller-ball topical oil applicator of FIG. 1.
Figure 3:
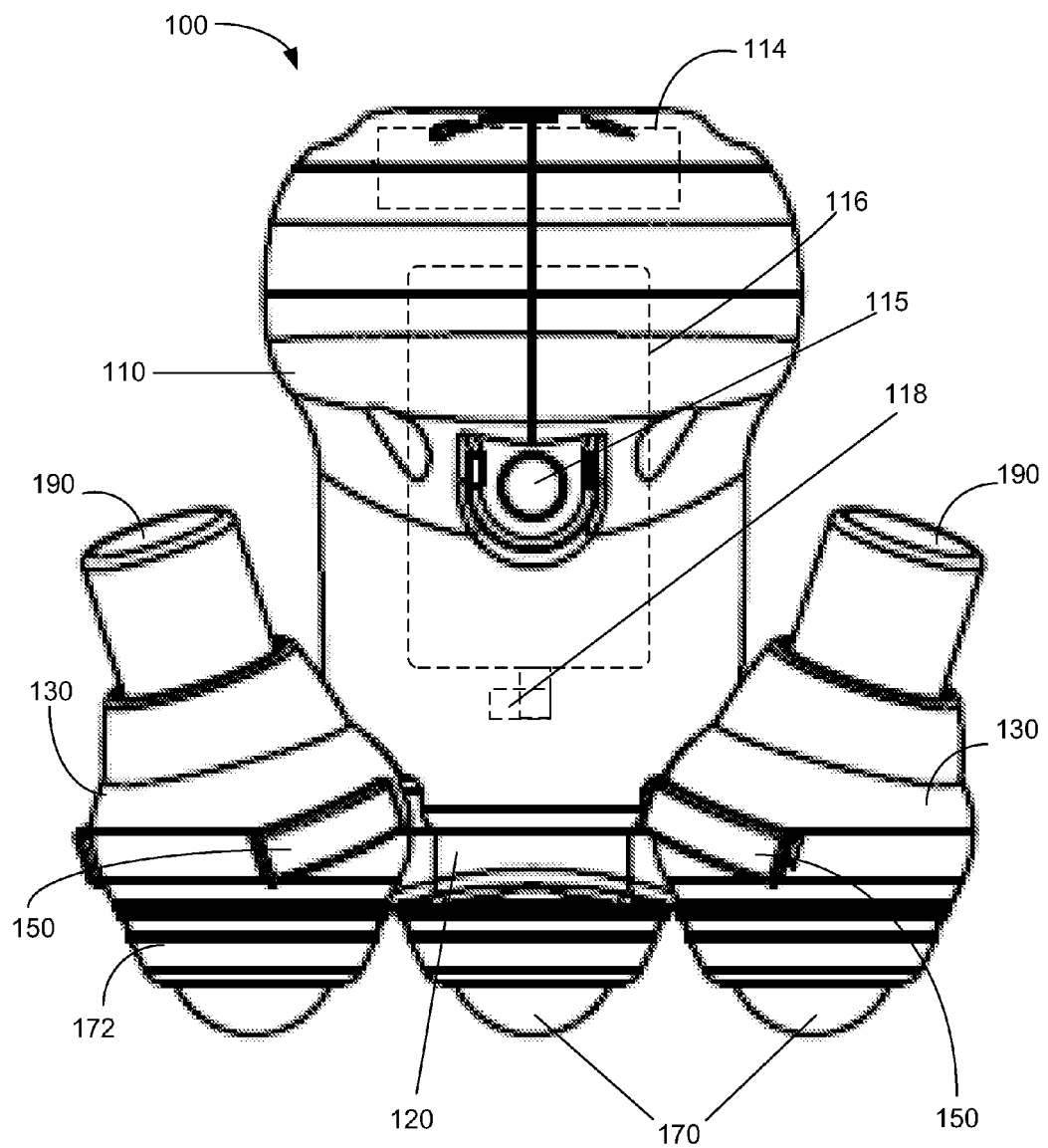
FIG. 3 illustrates a side view of the exemplary massaging multiple roller-ball topical oil applicator of FIG. 1.

FIGS. 1-3 illustrate massaging multiple roller-ball topical oil applicator 100, which may be used for massaging and for applying topical oils, such as essential oils to the skin of an individual or other creature. Applicator 100 may include body 110, base 120, and roller-ball feet 130, along with oil containers 190. As is shown in the figures, applicator 100 may include three roller-ball feet 130. In other embodiments, applicator 100 may include one or more roller-ball feet 130. Each of roller-ball feet 130 may include flow switch 150 and roller-ball 170, each of which will be described in further detail below.

Body 110 may include top cover 112 and switch 115. Body 110 may be formed in an ergonomic shape to conform with and be comfortable for a human hand to grasp and use. Body 110 may be formed of any suitable material, such as metal, plastic, wood, or any combination of or composite material. For example, body 110 may be formed of plastic and covered (at least partially) by a vibration dampening and pliable sleeve (not shown), such as of neoprene. Body 110 may be formed a sufficient size and configuration to accommodate a vibration assembly and to allow for bottles 190 to be selectively removed from roller-ball feet 130.

As best shown in FIG. 3, within body 110 may be located a vibration assembly with batteries 114, motor 116 and eccentric mass 118. Top cover 112 of body 110 may be a battery compartment access door such that top cover 112 may be removed to replace batteries 114. Eccentric mass 118 may rotate when motor 116 is turned on with switch 115, causing vibrations due to the unbalanced rotation of eccentric mass 118. In some embodiments, a control board may be used to control different speeds or functions of the vibration assembly. Similarly, the vibration assembly may be powered with a cord instead of batteries 114, or may include a power management circuit that may be used to charge batteries 114. Similarly, in any embodiment of applicator 100, any suitable massaging or vibration mechanism may be used to provide applicator 100 with a massaging action.

Base 120 may be coupled to body 110 and to roller-ball feet 130. Base 120 may be coupled to body 110 with fasteners, such as screws, or may be permanently coupled to body 110 with sonic welding, adhesives, etc. Base 120 may be formed of any suitable material to withstand the forces of having a person push down on body 110 to apply roller-ball feet to give a massage to an individual person or creature. Similarly, base 120 may be formed of an oil-resistant material to resist degradation by oils used with applicator 100. For example, base 120 may be formed of certain plastics, metal, ceramic, composites, wood, or any combination of these and other suitable materials.

Figure 4:
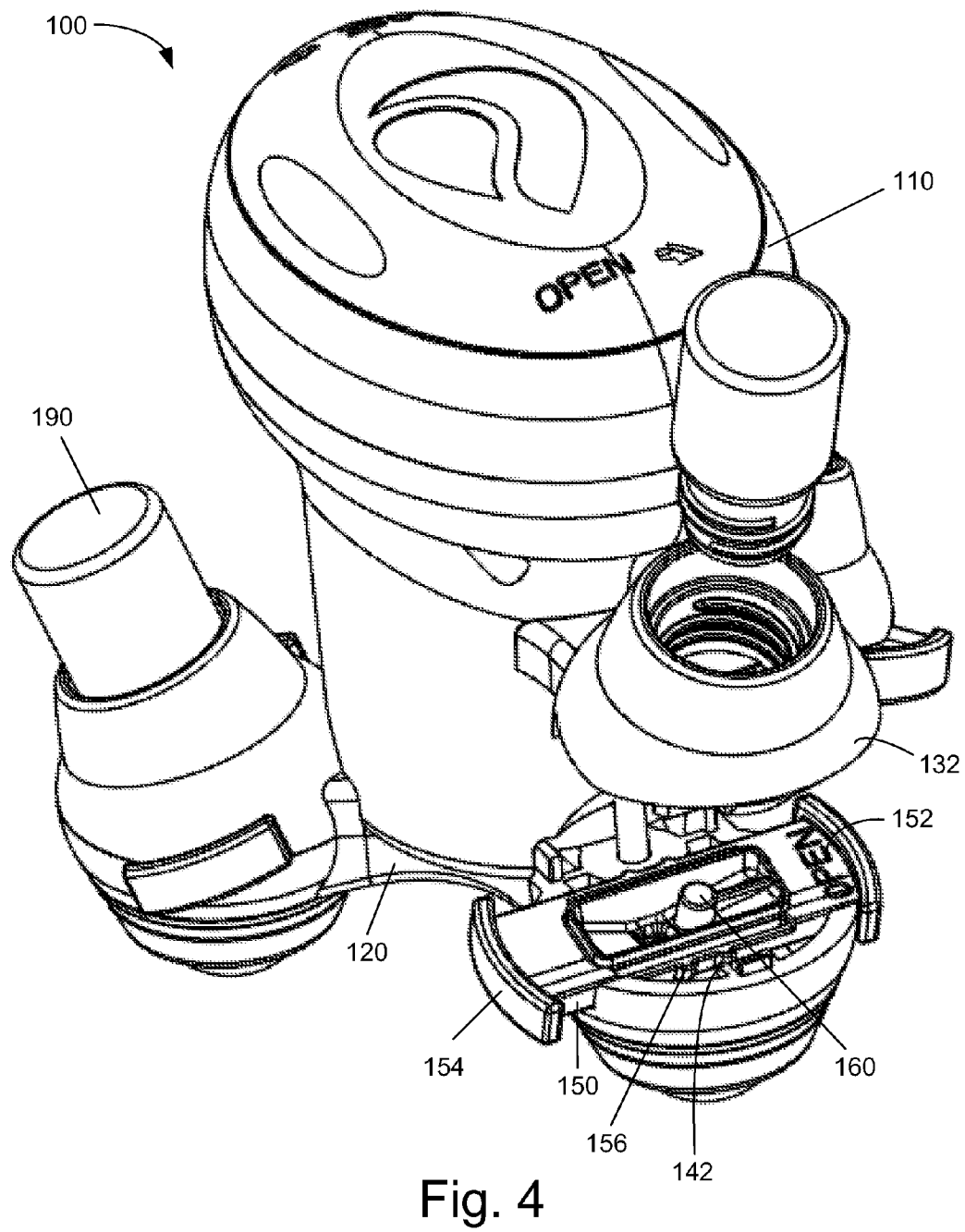
FIG. 4 illustrates a partial exploded view of an exemplary massaging multiple roller-ball topical oil applicator.
Figure 5:
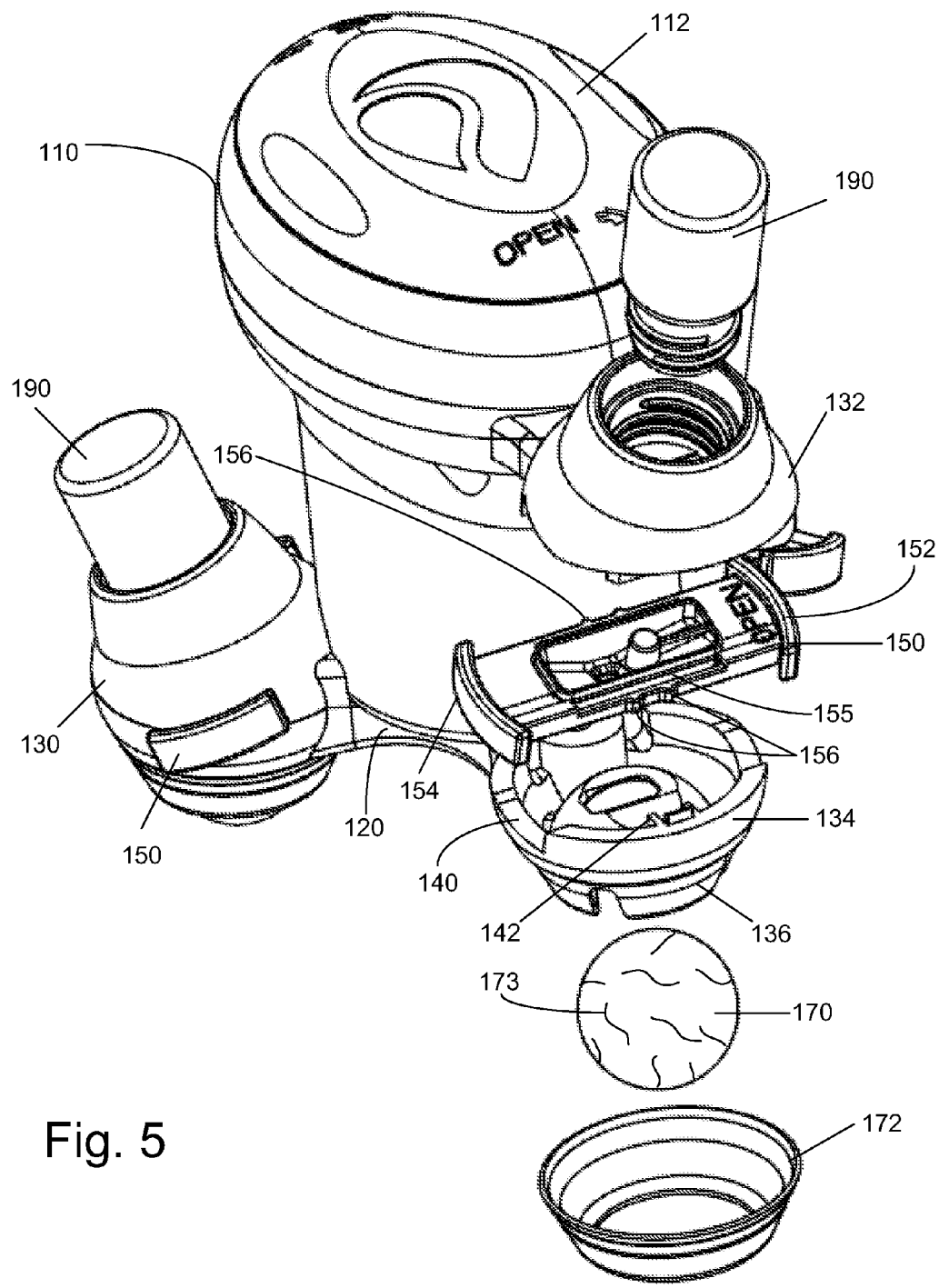
FIG. 5 illustrates a partial exploded view of an exemplary massaging multiple roller-ball topical oil applicator.

FIGS. 4-5 illustrate exploded views of roller-ball foot 130. Roller-ball foot 130 may be formed of any suitable material for use with a massaging essential oil applicator. For example, roller-ball foot 130, along with any other component of applicator 100 that may be in contact with essential oils dispensed from applicator 100, may be formed from an oil resistant plastic or other suitable material such as chemically resistant polypropylene, ultem, other homopolymers, etc., or other suitable materials, including materials with oil resistant coatings. Roller-ball foot 130 may include top 132, roller-ball housing 134, and ball socket 136, configured to accommodate roller-ball 170 and retaining ring 172. In some embodiments, roller-ball housing 134 may be formed as a portion of base 120, while in other embodiments, roller-ball housing 134 may be coupled to base 120 using any suitable fastener, adhesive, coupling or joining method.

Figure 6:
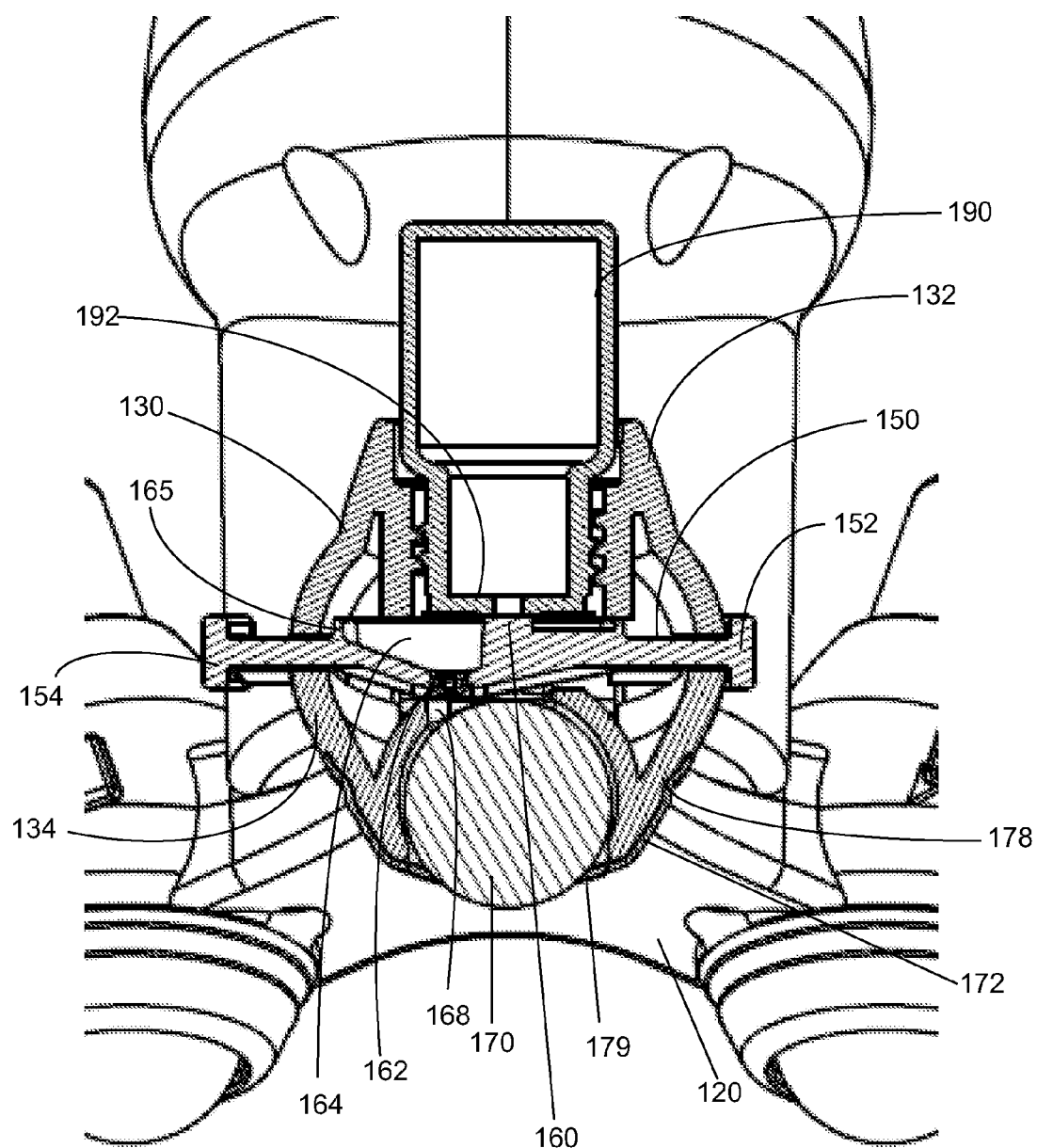
FIGS. 6 and 7 illustrate a cross-sectional views of an exemplary massaging multiple roller-ball topical oil applicator.

As best shown in FIG. 6, roller-ball housing 134 may also include a groove 178 for holding and working in conjunction with retaining ring 172 to hold roller-ball 170 in place in order to apply topical oil. Retaining ring 172 may include ball retainer lip 179, defining a hole in retaining ring 172 through which a portion of roller-ball 170 may extend. Retainer lip 179 may have an annular diameter dimension smaller than the diameter of roller-ball 170 to secure roller-ball 170 in place without allowing roller-ball 170 to pass through retaining ring 172 when attached to roller-ball housing 134. Retaining ring 172 may also include an indent to cooperate with grove 178 of roller-ball housing 134 to hold retaining ring 172 in place on roller-ball foot 130, thereby holding roller-ball 170 in place. In some embodiments, roller-ball 170 may be held in place with a portion of roller-ball housing 134 with retaining ring 172 securing roller-ball 170 in roller-ball foot 130, such that the materials of roller-ball foot 130 may not relax beyond the dimensions of retaining ring 172.

Retaining ring 172 may be formed of any suitable material to resist relaxation of roller-ball housing 134 if essential oils penetrate the material of roller-ball housing 134, thereby keeping roller-ball 170 in place. Such materials may include metals, such as aluminum, steel, copper, brass, titanium, or any suitable alloy from these or other metals. Such materials may also include ceramics, carbon fiber, or any other suitable material. In some embodiments retaining ring 172 may be coated or treated to resist corrosion, including, for example, anodizing, Teflon coating, enamel, etc.

Roller-ball 170 may be placed in roller-ball housing 134 and then retaining ring 172 may be placed onto roller-ball housing 134. By pressing retaining ring 172 over the lower portion of roller-ball housing 134, indent 178 of retaining ring 172 may snap into place in the groove at an appropriate depth to hold roller ball 170 in place, while also providing appropriate spacing to allow a desired flow of essential oils to be applied with applicator 100. As such, at least one of roller-ball housing 134 and retaining ring 172 may be formed of a material that allows for elastic deformation to permit retaining ring 172 to be fitted over roller-ball housing 134 as described and illustrated. Roller-ball 170 may be formed in any suitable size for use as a massaging implement. Similarly, roller-ball 170 may be sized relative to roller-ball housing 134 to control the flow rate of oil. For example, a tighter fitting roller-ball 170 would allow a slower flow rate than a looser fitting roller-ball 170.

Essential oils such as citrus oils, frankincense, oils high in monoterpenes or blends of such oils mixed with other solvents, tend to affect plastics in an aggressive manner. Retaining ring 172 fitted over roller-ball housing 134 may allow roller-ball housing 134 to be formed of a plastic material that is suitable for use in an aggressive oils environment without losing roller-ball 170. Similarly, roller-ball 170 may be formed of any suitable material sufficient to maintain a desired fit and alignment with roller-ball foot 130 to provide a desired flow-rate of oil at each application. For example, roller-ball 170 may be formed of steel, aluminum, ceramic, or any other suitable material.

Slot 140 may be formed in roller-ball foot 130 to accommodate flow switch 150. Notches 142 may be provided in roller-ball foot 130 to work with protrusions 156 of flow switch 150 to achieve a detent action to hold flow switch 150 in a desired open or closed position. Top 132 and roller-ball housing 134 may be coupled together to form slot 140 and hold fluid switch 150 in place by sonic welding, fasteners, glue, or any other suitable component coupling method.

Figure 7:
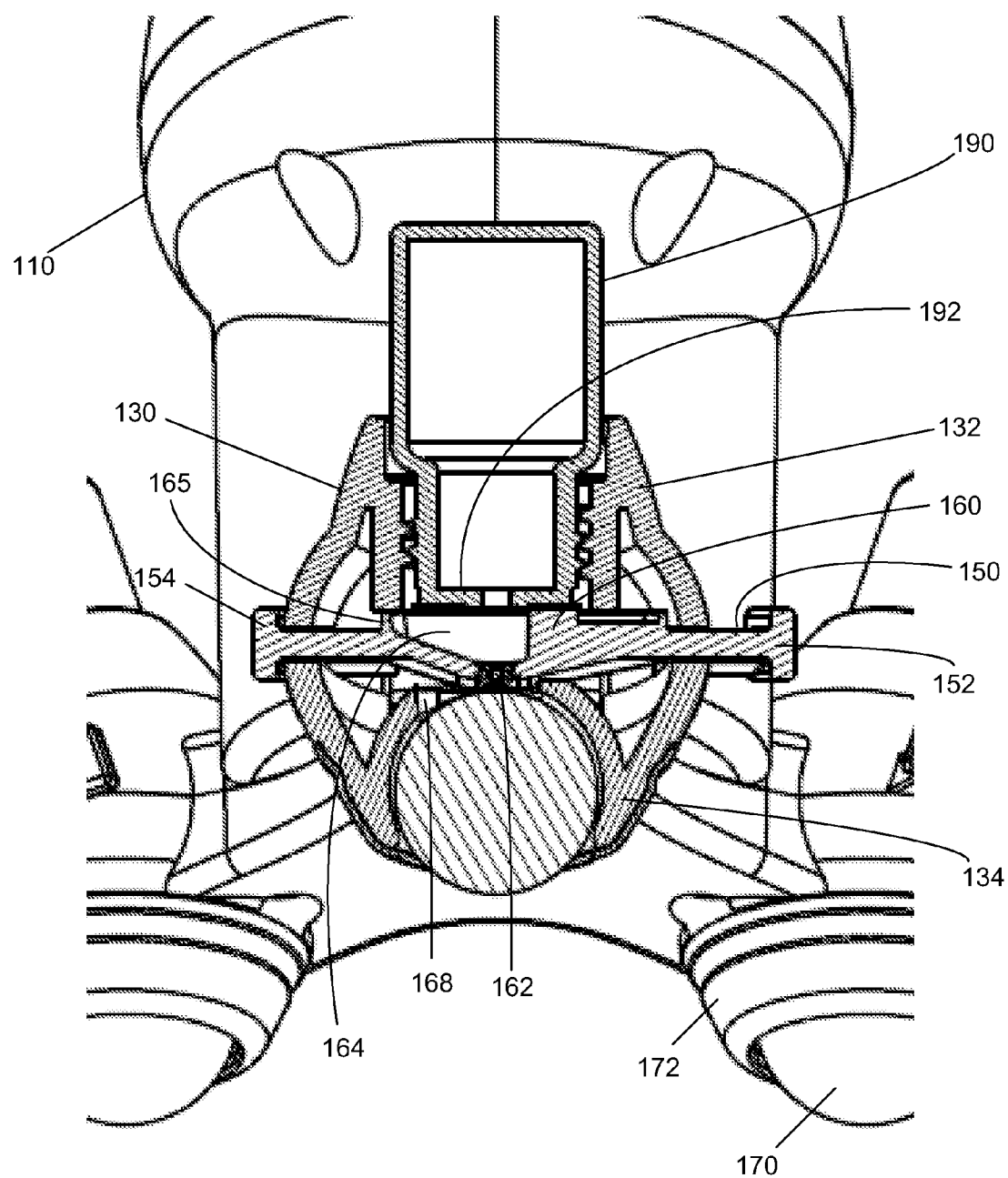

Flow switch 150 may include first end 152 and second end 154. Stopper 160 and well 164 may also be formed in flow switch 150. Channel 162 may be formed in well 164 of flow switch 150. As mentioned above, protrusions 156 may be formed on the sides of flow switch 150 to provide a detent mechanism to hold flow switch in one of an open position, as shown in FIG. 7 or a closed position, as shown in FIG. 6. Slot 155 may be formed in flow switch 150 to provide resilience for protrusions 156 to push past notches 142 of roller-ball foot 130.

First end 152 of flow switch 150 may include the word "open" printed or formed on a portion of first end 152. Similarly, first end 152 may be colored green (or any other color to signify as being open), and second end 154 may be colored red or some other color to indicate that the flow is closed. As shown best in FIGS. 6 and 7, flow switch 150 may be moved between an open position (FIG. 7) and a closed position (FIG. 6). In the open position, well 164 may be positioned below an opening in flow insert 192 of bottle 190, allowing fluid to flow from bottle 190 into well 164, through channel 162, and onto roller-ball 170 to be dispensed from roller-ball 170 onto any surface against which roller-ball 170 is rolled, such as human skin. In the open position, first end 152 extends from roller-ball foot 130, revealing the "open" indicia or the green color, indicating that oil may pass from bottle 190 to roller-ball 170 to be dispensed. In the open position, stopper 160 may be positioned away from the opening in bottle insert 192, and seal 165 may be positioned against a portion of top 132 to prevent oil from spilling out of well 164 and into top 132.

When flow switch 150 is positioned in a closed position, stopper 160 may be positioned over the opening in flow insert 192 of bottle 190. As such, oil may be prevented from exiting bottle 190. In the closed positioned, well 164 may be positioned such that any oil remaining in well 164 may flow through channel 162 and passage 168 to be dispensed by roller-ball 170. In either case, applicator 100 may be used in any orientation as a massager, with the orientation being used at times to help regulate the flow rate of oils, as desired.

In order to attach bottles 190 to applicator 100, applicator may be positioned upside down to keep the bottles 190 upright. The bottles 190 may be screwed into receiving positions in each of the top 132 portions of the roller-ball feet 130. As shown in the figures, the bottles may be oriented at a slight angle from vertical to accommodate the proximity of roller-ball feet 130 and an ease of attaching bottles 190. After each of the bottles (or as many bottles as desired) are seated in top 132 portions, the applicator may be used to massage and dispense oils as desired.

In some embodiments, flow insert 192 may be formed such that even when bottle 190 is held upside down, there is very low, if any flow. In such embodiments, applicator 100 would not need to be inverted to place or exchange bottles 190 one for another. In such embodiments, the flow of fluid from bottle 190 would correspond to when the vibration assembly is vibrating, the vibrations facilitating the flow through flow insert 192. As such, in some embodiments, turning on and off switch 115 may control flow of fluids from any of bottles 190. Similarly, the opening in flow insert 192 may be sized to achieve a desired flow rate when in use. For example, a larger opening may provide a faster flow rate and a smaller opening, a lower flow rate.

Bottles 190 may be any container suitable to hold essential oils. Bottles 190 may be formed of glass, metal, plastic, or any other suitable material. Bottles 190 may be removably coupled to roller-ball feet 130 using threads as shown in the figures, or with a clamping mechanism, camming locks, or any other method of attaching a fluid container to an applicator.

In the illustrated embodiments, three roller-ball feet 130 are shown. As discussed, each of the roller-ball feet 130 may have a bottle 190 with oils to be used with applicator 100 is providing a massage. Because there are multiple positions for bottles, different combinations of oils or other fluids may be used with applicator 100. For example, some oil other than an essential oil, such as a mineral oil, baby oil, nut or fruit oil, or vegetable oil may be in one of the bottles 190, while eucalyptus essential oils are in the remaining two bottles 190. Similarly, one or more of the bottles may be empty or not positioned initially such that only one or none of the roller-ball feet 130 is able to dispense oil at any given time.

Similarly, the flow switch 150 for each of the roller-ball feet 130 may be selectively open or closed to provide a desired oil application during a massage. In some embodiments, a specific treatment pattern using different essential oils may be easily affected by keeping two flow switches closed and opening the flow switch 150 of a first desired oil. When enough of the first desired oil is dispensed, or the first oil is depleted, the flow switch 150 of the first desired oil may be closed, and the flow switch 150 of a second desired oil may be opened, and so on. In some embodiments, different combinations of oils may be used to achieve a particular therapy or outcome simultaneously, depending on the order and combinations the oils are used.

In some embodiments, roller-ball 170 may include surface features 173 (FIG. 5) that may facilitate collecting oils onto roller-ball 170 when being used, and may also provide additional tactile stimulation when used during a massage. In some embodiments, surface features 173 may be various patterns or designs, such as with a company logo, geometric pattern, or other desired aesthetic feature that also serves to carry oil. Surface features 173 may be formed in or on the surface of roller-ball 170 through any method, such as etching, cutting, grinding, micro-welding, casting, stamping, etc. In some embodiments, a single bottle may be in fluid communication with and be used to supply oil to more than one roller-ball foot 130, such as through a tube.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, examples are meant to be illustrative only and should not be construed to be limiting in any manner.

The invention claimed is:

1. A method of applying topical oil to an individual, the method comprising:
   placing topical oil in a plurality of containers;
   coupling each one of the plurality of containers to a top of a respective one of a plurality of roller-ball feet, wherein each roller-ball foot is affixed to a body and has a roller-ball disposed within a roller-ball cavity, wherein a longitudinal axis of each one of the plurality of containers is coplanar with a diameter of a respective one of the roller-balls, wherein each one of the plurality of containers is external to the body and in fluid communication with a respective one of the plurality of roller-ball feet via a respective one of a plurality of flow switches, wherein each one of the plurality of flow switches is configured to independently control fluid flow of the topical oil for each respective roller-ball foot;

placing the roller-ball of at least a selected one of the plurality of roller-ball feet against the skin of an individual;

actuating the flow switch of the selected one of the roller-ball feet to allow fluid flow of the topical oil from the respective container to the roller-ball that is against the skin of the individual;

activating a vibration assembly to apply massaging vibrations through the roller-ball to the individual; and moving the plurality of roller-ball feet such that the roller-ball delivers oil to the skin of the individual.

2. The method of claim 1, wherein, the plurality of containers is three containers, and the plurality of roller-ball feet is three roller-ball feet.

3. The method of claim 1, wherein the topical oil in each of the plurality of containers is an essential oil.

4. The method of claim 3, wherein the essential oil in one of the plurality of containers is different from the essential oil in another one of the plurality of containers.

5. The method of claim 1, wherein the plurality of topical oil containers are formed from glass.

6. The method of claim 1, wherein the topical oil comprises a citrus essential oil.

7. The method of claim 1, wherein the topical oil comprises a frankincense essential oil.

8. The method of claim 1, further comprising turning off the massaging vibrations.

9. A device for applying topical oils to an individual, the device comprising:

a body;

a vibration assembly disposed within the body;

a plurality of roller-ball feet coupled to the body, wherein each roller-ball foot comprises a roller-ball disposed within a roller-ball cavity;

a plurality of containers configured to hold topical oil, wherein each one of the plurality of containers is external to the body and detachably coupled to a top of and in fluid-providing communication with a respective one of the plurality of roller-ball feet, wherein a longitudinal axis of each one of the plurality of containers is coplanar with a diameter of a respective one of the roller-balls; and a plurality of flow switches, wherein each one of the plurality of flow switches is coupled between the roller-ball cavity of a respective one of the plurality of roller-ball feet and a respective one of the plurality of containers, wherein each one of the plurality of flow switches is configured to independently control fluid flow of the topical oil for each respective roller-ball foot.

* * * * *